(12) United States Patent
Chang et al.

(10) Patent No.: US 7,842,803 B2
(45) Date of Patent: Nov. 30, 2010

(54) NICOTINIC ACETYLCHOLINE RECEPTOR LIGANDS 101

(75) Inventors: Hui-Fang Chang, Wilmington, DE (US); Christopher Holmquist, Wilmington, DE (US); Eifion Phillips, Boothwyn, PA (US); Timothy Piser, Wilmington, DE (US); Thomas Simpson, Wilmington, DE (US); Rebecca Urbanek, Wilmington, DE (US); James Woods, Wilmington, DE (US); Hui Xiong, Wilmington, DE (US)

(73) Assignee: AstraZeneca AB (SE)

( * ) Notice: Subject to any disclaimer, the term of this patent is extended or adjusted under 35 U.S.C. 154(b) by 724 days.

(21) Appl. No.: 11/749,820

(22) Filed: May 17, 2007

(65) Prior Publication Data

US 2008/0139600 A1    Jun. 12, 2008

Related U.S. Application Data

(60) Provisional application No. 60/747,476, filed on May 17, 2006, provisional application No. 60/824,975, filed on Sep. 8, 2006.

(51) Int. Cl.
*C07D 265/30* (2006.01)
*A61K 31/5375* (2006.01)

(52) U.S. Cl. .............. 544/106; 546/18; 514/231.2; 514/278

(58) Field of Classification Search .......... 540/106; 546/18; 514/231.2, 278
See application file for complete search history.

(56) References Cited

FOREIGN PATENT DOCUMENTS

| WO | WO 9903859 | * | 1/1999 |
|----|------------|---|--------|
| WO | 02096912   |   | 12/2002 |
| WO | 03087102 A1 |   | 10/2003 |
| WO | 03087103 A1 |   | 10/2003 |
| WO | 03087104 A1 |   | 10/2003 |
| WO | 2005030778 A1 |   | 4/2005 |

OTHER PUBLICATIONS

English Abstract DN 121:222102 Jennifer Court et al , 1994.*
International Search Report from PCT/SE2007/000485 dated Sep. 5, 2007.

* cited by examiner

*Primary Examiner*—Rita J Desai
(74) *Attorney, Agent, or Firm*—Connolly Bove Lodge & Hutz, LLP

(57) ABSTRACT

Nicotinic acetylcholine receptor ligands of Formula I wherein X, n, $R^1$ and $R^2$ are as described in the specification, diastereoisomers, enantiomers, pharmaceutically-acceptable salts, methods of making, pharmaceutical compositions containing, and methods for using the same.

4 Claims, No Drawings

NICOTINIC ACETYLCHOLINE RECEPTOR LIGANDS 101

RELATED APPLICATIONS

This application claims the benefit of U.S. Provisional Application No. 60/747,476, filed May 17, 2006, and U.S. Provisional Application No. 60/824,975, filed Sep. 8, 2006.

FIELD OF THE INVENTION

This invention relates to furopyridine compounds or pharmaceutically-acceptable salts thereof, processes for preparing them, pharmaceutical compositions containing them and their use in therapy. The invention relates to compounds that bind to nicotinic acetylcholine receptors (nAChRs) and particularly to compounds that bind to alpha-7 nicotinic acetylcholine receptors.

BACKGROUND OF THE INVENTION

Schizophrenia, clinical anxiety and depression daily affect many millions of people. These conditions are brain disorders that have serious and lasting effects on people's lives and impact the sufferers and their friends and relatives.

People with schizophrenia often have trouble thinking clearly or making decisions. They may have a hard time telling real life from fantasy. They may have so-called positive symptoms such as delusions or hallucinations which they experience but which do not reflect reality, and see or believe things that are not real; or they may have negative symptoms and lack behaviors or feelings that normal people have, avoid social contact and be emotionally withdrawn. Often they start to do things, but not follow through and take no pleasure or interest in life; they may be confused in thinking and speech and act in ways that do not make sense.

People who have generalized anxiety disorder (GAD) worry excessively and uncontrollably about everyday things. This constant worry affects daily functioning and physical symptoms can include sweating, nausea, gastrointestinal discomfort or diarrhea. Sufferers tend to be irritable and complain about feeling on edge, are easily tired and have trouble sleeping. GAD can occur with other anxiety disorders, depressive disorders, or substance abuse. The intensity, duration and frequency of worrying varies but is disproportionate to the issue and interferes with the sufferer's performance of tasks and ability to concentrate.

Depressive disorder is an illness that involves the body, mood, and thoughts. It affects the way a person eats and sleeps, the way they feel about themselves, and the way they think about things. People with a depressive illness cannot merely "pull themselves together" and get better. Without treatment, symptoms can last for weeks, months, and even years. Major depression interferes with a person's ability to work, study, sleep, eat, and enjoy life. A disabling episode of depression may occur only once but more commonly occurs several times in a lifetime. A less severe type of depression, termed dysthymia, involves long-term, chronic symptoms that do not disable, but keep one from functioning well or from feeling good. Many people with dysthymia also experience major depressive episodes at some time in their lives. Bipolar disorder is yet another type of depression that is also called manic-depressive illness. It is not as prevalent as other forms of depressive disorders and bipolar disorder is characterized by cycling mood changes that swing between manic highs and depressive lows. Sometimes the mood switches are dramatic and rapid, but most often they are gradual. When in the depressed phase, a person can have any or all of the symptoms of a depressive disorder. When in the manic phase, a person may be overactive, overtalkative, and have a great deal of energy. Manic persons often think differently and their judgment and social behavior changes in ways that cause serious problems and embarrassment; they may feel elated, have grand schemes, make unwise business decisions and indulge in romantic sprees. Untreated mania can also evolve into a psychotic state.

Schizophrenia, clinical anxiety and depression are brain disorders thought to arise from the overactivity, underactivity or imbalanced activity of brain cells. Activities of brain cells and all thinking and feeling are thought to result from the activities of different brain messengers interacting with receptors on brain cells. Acetylcholine is one of several messengers by which brain cell communicate with each other. Acetylcholine interacts with numerous kinds of receptors some of which are the nicotinic acetylcholine receptors that are susceptible to the actions of nicotine found in tobacco. The use of compounds which bind nicotinic acetylcholine receptors in the treatment of a range of disorders including schizophrenia, anxiety and depression, Alzheimer's disease, cognitive or attention disorders, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; and in Williams et al. (1994) "Neuronal Nicotinic Acetylcholine Receptors," Drug News & Perspectives, vol. 7, pp. 205-223.

Various nicotinic acetylcholine receptors are known, but one of particular interest is the alpha-7 nicotinic acetylcholine receptor and compounds targeting the alpha-7 receptor are thought to be particularly beneficial for treating schizophrenia, anxiety and depression.

DESCRIPTION OF THE INVENTION

This invention concerns nicotinic acetylcholine receptor-active compounds according to Formula I:

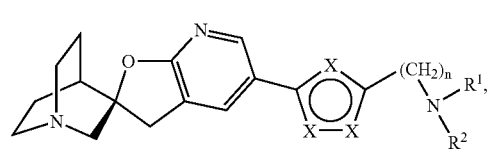

I wherein:

X is independently selected at each occurrence from CH, O, S, N or NH and at least one X is selected from O, S, N or NH and not more than one X is O or S;

n is, 0, 1, 2, or 3, and $R^1$ and $R^2$ are independently selected at each occurrence from hydrogen, —$C_{1-6}$alkyl, —$C_{3-7}$cycloalkyl, —$C_{2-6}$alkenyl, —$C_{2-6}$alkynyl, —$CF_3$, —$CONR^3R^4$, —$CH_2NR^3R^4$ or —$CH_2OR^3$;

or, $R^1$ and R2 together with the nitrogen to which they are attached form a 5- or 6-membered heteroaromatic ring having as ring atoms 1, 2 or 3 heteroatoms selected from nitrogen, oxygen and sulfur, or a 5- or 6-membered heterocyclic ring having as ring atoms 1, 2 or 3 heteroatoms selected from nitrogen, oxygen and sulfur;

where $R^3$ and $R^4$ are independently selected at each occurrence from hydrogen or —$C_{1-4}$alkyl, and where any alkyl, cycloalkyl, alkenyl or alkynyl moiety may be substituted with 1, 2, 3 or more halogen, —OH or ═O moieties as chemically feasible.

The invention also encompasses stereoisomers, enantiomers, in vivo-hydrolysable precursors and pharmaceutically-acceptable salts of compounds of Formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes. Compounds described herein selectively bind to alpha-7 nicotinic acetylcholine receptors and thus are particularly useful for treating schizophrenia, anxiety and depression.

DETAILED DESCRIPTION OF THE INVENTION

Compounds are those according to Formula I:

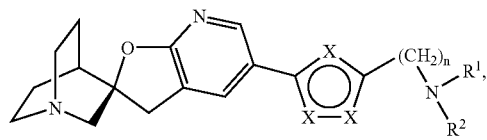

I wherein:

X is independently selected at each occurrence from CH, O, S, N or NH and at least one X is selected from O, S, N or NH and not more than one X is O or S;

n is, 0, 1, 2, or 3, and $R^1$ and $R^2$ are independently selected at each occurrence from hydrogen, —$C_{1-6}$alkyl, —$C_{3-7}$cycloalkyl, —$C_{2-6}$alkenyl, —$C_{2-6}$alkynyl, —$CF_3$, —$CONR^3R^4$, —$CH_2NR^3R^4$ or —$CH_2OR^3$;

or, $R^1$ and $R^2$ together with the nitrogen to which they are attached form a 5- or 6-membered heteroaromatic ring having as ring atoms 1, 2 or 3 heteroatoms selected from nitrogen, oxygen and sulfur, or a 5- or 6-membered heterocyclic ring having as ring atoms 1, 2 or 3 heteroatoms selected from nitrogen, oxygen and sulfur;

$R^3$ and $R^4$ are independently selected at each occurrence from hydrogen or —$C_{1-4}$alkyl, and where any alkyl, cycloalkyl, alkenyl or alkynyl moiety may be substituted with 1, 2, 3 or more halogen, —OH or ═O moieties as chemically feasible;

stereoisomers, enantiomers, in vivo-hydrolysable precursors and pharmaceutically-acceptable salts thereof.

Other compounds are those wherein the moiety

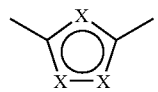

is selected from moieties of Formulae II, III, IV, V or VI

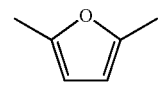

II

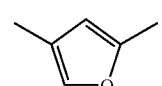

III

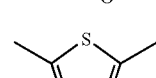

IV

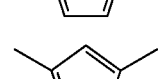

V

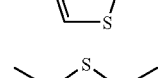

VI

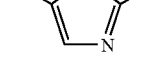

Other compounds are those wherein $R^1$ and $R^2$ are independently selected from hydrogen or methyl.

Other compounds are those wherein n is 1 or 2.

Yet other compounds are those wherein $R^1$ and $R^2$ together with the nitrogen to which they are attached are pyrrolidinyl, piperidinyl, piperazinyl or morpholinyl.

Still other compounds are those wherein the moiety

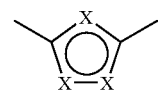

is selected from moieties of Formulae II, III, IV, V or VI,

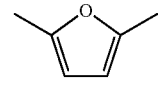

II

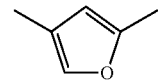

III

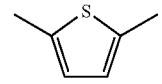

IV

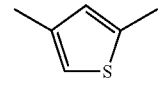

V

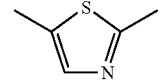

VI $R^1$ and R2 are independently selected from hydrogen or $C_{1-6}$alkyl, and n is 1 or 2.

Particular compounds are those wherein the moiety

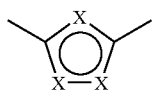

is selected from moieties of Formulae II or IV,

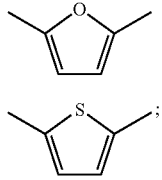

$R^1$ and $R^2$ are independently selected from hydrogen or $C_{1-4}$alkyl, and
n is 1 or 2.

Other particular compounds are those wherein the moiety

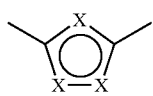

is of Formula II,

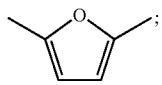

$R^1$ and $R^2$ are independently selected from hydrogen, methyl or ethyl, and
n is 1 or 2.

Particular compounds are those wherein the moiety

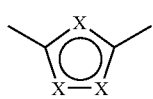

is of Formula IV,

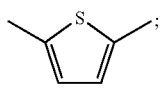

$R^1$ and $R^2$ are independently selected from hydrogen, methyl or ethyl, and
n is 1 or 2.

Particular compounds are those described herein and pharmaceutically-acceptable salts thereof.

Another aspect encompasses compounds according to Formula I wherein one or more of the atoms is a radioisotope of the same element. In a particular form of this aspect the compound of Formula I is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Compounds labeled with tritium are useful for the discovery of novel medicinal compounds that bind to and modulate the activity, by agonism, partial agonism, or antagonism, of the alpha-7 nicotinic acetylcholine receptor. Such tritium-labeled compounds may be used in assays that measure the displacement of such a compounds to assess the binding of ligand that bind to alpha-7 nicotinic acetylcholine receptors.

Another aspect relates to compounds according to Formula I and their use in therapy and to compositions containing them.

Yet another aspect encompasses the use of compounds according to Formula I for the therapy of diseases mediated through the action of nicotinic acetylcholine receptors. A more particular embodiment of this aspect relates to the use of compounds of Formula I for the therapy of diseases mediated through the action of alpha-7 nicotinic acetylcholine receptors.

Another aspect encompasses a method of treatment or prophylaxis of diseases or conditions in which activation of the alpha-7 nicotinic receptor is beneficial which method comprises administering a therapeutically-effective amount of a compound of Formula I to a subject suffering from said disease or condition.

One embodiment of this aspect is a method of treatment or prophylaxis, wherein the disorder is anxiety, schizophrenia, mania or manic depression.

Another embodiment of this aspect is a method of treatment or prophylaxis of neurological disorders, psychotic disorders or intellectual impairment disorders, which comprises administering a therapeutically effective amount of a compound of Formula I.

Another embodiment of this aspect is a method of treatment or prophylaxis, wherein the disorder is Alzheimer's disease, learning deficit, cognition deficit, attention deficit, memory loss, or Attention Deficit Hyperactivity Disorder.

Another embodiment of this aspect is a method of treatment or prophylaxis, wherein the disorder is Parkinson's disease, Huntington's disease, Tourette's syndrome, or neurodegenerative disorders in which there is loss of cholinergic synapses.

Another embodiment of this aspect is a method of treatment or prophylaxis of jetlag, nicotine addiction, craving, pain, and for ulcerative colitis, which comprises administering a therapeutically effective amount of a compound of Formula I.

Yet another embodiment of this aspect is a method for inducing the cessation of smoking that comprises administering an effective amount of a compound of Formula I.

Another embodiment of this aspect is a pharmaceutical composition comprising a compound of the invention and at least one pharmaceutically-acceptable diluent, lubricant or carrier.

A further aspect relates to a pharmaceutical composition useful for treating or preventing a condition or disorder mentioned herein arising from dysfunction of nicotinic acetylcholine receptor neurotransmission in a mammal, preferably a human, comprising an amount of a compound of Formula I, an enantiomer thereof or a pharmaceutically-acceptable salt thereof, effective in treating or preventing such disorder or condition, and at least one pharmaceutically-acceptable additive diluent, lubricant or carrier.

Another embodiment of this aspect relates to use of a pharmaceutical composition of the invention for the treatment, amelioration or prophylaxis of human diseases or conditions in which activation of the α7 nicotinic receptor is beneficial.

Another embodiment of this aspect is the use of the pharmaceutical composition a compound of Formula I for the treatment or prophylaxis of neurological disorders, psychotic disorders or intellectual impairment disorders.

Another embodiment of this aspect of the invention is the use of the pharmaceutical composition comprising a compound of Formula I for the treatment or prophylaxis of Alzheimer's disease, learning deficit, cognition deficit, attention deficit, memory loss, Attention Deficit Hyperactivity Disorder, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect is the use of a compound of Formula I, an enantiomer thereof or a pharmaceutically-acceptable salt thereof, in the manufacture of a medicament for the treatment or prophylaxis of the diseases or conditions mentioned herein.

Another embodiment of this aspect is the use of a compound of Formula I in the manufacture of a medicament for the treatment or prophylaxis of human diseases or conditions in which activation of the alpha-7 nicotinic receptor is beneficial.

Another embodiment of this aspect is the use of a compound of Formula I in the manufacture of a medicament for the treatment or prophylaxis of neurological disorders, psychotic disorders or intellectual impairment disorders.

Another embodiment of this aspect is the use of a compound of Formula I in the manufacture of a medicament for treatment or prophylaxis of Alzheimer's disease, learning deficit, cognition deficit, attention deficit, memory loss or Attention Deficit Hyperactivity Disorder.

Another embodiment of this aspect is the use of a compound of Formula I in the manufacture of a medicament for treatment or prophylaxis of anxiety, schizophrenia, or mania or manic depression.

Another embodiment of this aspect is the use of a compound of Formula I in the manufacture of a medicament for treatment or prophylaxis of Parkinson's disease, Huntington's disease, Tourette's syndrome, or neurodegenerative disorders in which there is loss of cholinergic synapses.

Another embodiment of this aspect is the use of a compound of Formula I in the manufacture of a medicament for the treatment or prophylaxis of jetlag, pain, or ulcerative colitis.

Another aspect relates to the use of a compound of Formula I in the manufacture of a medicament for facilitating the cessation of smoking or the treatment of nicotine addiction or craving including that resulting from exposure to products containing nicotine.

Another aspect relates to the use of a compound of Formula I in combination with other therapeutically-active compounds or substances in pharmaceutical compositions or formulations, methods to treat diseases and conditions, uses as medicaments and uses in the manufacture of medicaments. Particular embodiments of this aspect comprise other therapeutically-active compounds or substances selected from sedatives, hypnotics, anxiolytics, antipsychotics, antianxiety agents, tranquilizers, and the like.

For the uses, methods, medicaments and pharmaceutical compositions mentioned herein the amount of compound used and the dosage administered will, of course, vary with the compound employed, the mode of administration and the treatment desired. However, in general, satisfactory results are obtained when the compounds of Formula I are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carriers, lubricants and diluents.

The compounds of Formula I, an enantiomer thereof, and pharmaceutically-acceptable salts thereof, may be used on their own or in the form of appropriate medicinal preparations for enteral or parenteral administration. According to a further aspect there is provided a pharmaceutical composition including preferably less than 80% and more preferably less than 50% by weight of a compound of Formula I in admixture with an inert pharmaceutically-acceptable diluent, lubricant or carrier.

Examples of diluents, lubricants and carriers are:
- for tablets and dragees: lactose, starch, talc, stearic acid;
- for capsules: tartaric acid or lactose;
- for injectable solutions: water, alcohols, glycerin, vegetable oils;
- for suppositories: natural or hardened oils or waxes.

There is also provided a process for the preparation of such a pharmaceutical composition which process comprises mixing the ingredients.

Compounds described herein are agonists of nicotinic acetylcholine receptors. While not being limited by theory, it is believed that agonists of the alpha-7 nicotinic acetylcholine receptor (nAChR) subtype are useful in the treatment or prophylaxis of neurological disorders, psychotic disorders and intellectual impairment disorders. The compounds described herein are indicated as pharmaceuticals, in particular in the treatment or prophylaxis of neurological disorders, psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. Compounds described herein may also be useful as analgesics in the treatment of pain, chronic pain, and in the treatment or prophylaxis of Parkinson's disease, Huntington's disease, Tourette's syndrome, and neurodegenerative disorders in which there is loss of cholinergic synapses.

Compounds may further useful for the treatment or prophylaxis of jetlag, for use in inducing the cessation of smoking, craving, and for the treatment or prophylaxis of nicotine addiction including that resulting from exposure to products containing nicotine.

It is also believed that compounds described herein are useful in the treatment and prophylaxis of ulcerative colitis.

A compound of Formula I or a pharmaceutically acceptable salt, solvate or in vivo hydrolysable ester thereof, or a pharmaceutical composition or formulation comprising a compound of Formula I may be administered concurrently, simultaneously, sequentially or separately with another pharmaceutically active compound or compounds selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including for example carbamazepine, valproate, lamotrogine, gabapentin and equivalents and pharmaceutically active isomer(s) and metabolite(s) thereof;

(vi) Alzheimer's therapies including for example donepezil, memantine, tacrine and equivalents and pharmaceutically active isomer(s) and metabolite(s) thereof;

(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including for example abciximab, activase, NXY-059, citicoline, crobenetine, desmoteplase, repinotan, traxoprodil and equivalents and pharmaceutically active isomer(s) and metabolite(s) thereof;

(x) urinary incontinence therapies including for example darafenacin, falvoxate, oxybutynin, propiverine, robalzotan, solifenacin, tolterodine and and equivalents and pharmaceutically active isomer(s) and metabolite(s) thereof;

(xi) neuropathic pain therapies including for example gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including for example allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, zolpidem and equivalents and pharmaceutically active isomer(s) and metabolite(s) thereof, or (xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in the publication reference.

The compounds described herein have the advantage that they may be less toxic, be more efficacious, be longer acting, have a broader range of activity, be more potent, produce fewer side effects, are more easily absorbed or have other useful pharmacological properties.

As used herein, unless otherwise indicated, "$C_{1-6}$alkyl" includes $C_{1-4}$alkyl groups but is not limited to methyl, ethyl, n-propyl, n-butyl, i-propyl, i-butyl, t-butyl, s-butyl moieties, whether alone or part of another group, $C_{1-4}$alkyl groups may be straight-chained or branched, and $C_{3-4}$alkyl groups include cyclic alkyl moieties such as cyclopropyl and cyclobutyl.

As used herein, unless otherwise indicated, "$C_{2-6}$alkenyl" includes $C_{2-4}$alkenyl but is not limited to 1-propenyl, 2-propenyl, 1-butenyl, 2-butenyl and 3-butenyl.

As used herein, unless otherwise indicated, "$C_{2-6}$alkynyl" includes $C_{2-4}$alkynyl but is not limited to ethynyl, 1-propynyl, 2-propynyl, 1-butynyl, 2-butynyl and 3-butynyl.

As used herein, unless otherwise indicated, aryl refers to a phenyl ring that may have 1, 2 or 3 substituents selected from: halogen, $C_{1-4}$alkyl, $C_{2-4}$alkenyl, $C_{2-4}$alkynyl, $C_{1-4}$alkyl, CN, $NO_2$, and $CF_3$.

As used herein, unless otherwise indicated, heteroaryl refers to a 5- or 6-membered heteroaromatic ring having 1, 2 or 3 heteroatoms selected from nitrogen, oxygen and sulfur, and heterocyclyl refers to a 5- or 6-membered heterocyclic ring having 1, 2 or 3 heteroatoms selected from nitrogen, oxygen and sulfur, provided that such heteroaromatic or heterocyclic rings contains at least one nitrogen, oxygen, or sulfur atom.

As used herein, unless otherwise indicated, halogen refers to fluorine, chlorine, bromine, or iodine.

Where necessary, hydroxy, amino, or other reactive groups may be protected using a protecting group as described in the standard text "Protecting groups in Organic Synthesis", $3^{rd}$ Edition (1999) by Greene and Wuts.

Unless otherwise stated, reactions are conducted under an inert atmosphere, preferably under a nitrogen atmosphere and are usually conducted at a pressure of about one to about three atmospheres, preferably at ambient pressure (about one atmosphere).

Compounds and intermediates may be isolated from their reaction mixtures by standard techniques.

Acid addition salts of the compounds of Formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of Formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of Formula I may exist in tautomeric or enantiomeric forms, all of which are included within the scope. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions that will not cause racemisation.

Pharmacology

The pharmacological activity of compounds of the invention may be measured by using tests such as those set out below:

Assay for Affinity at an $\alpha_7$ nAChR Receptor by Measuring the Binding of $^{125}$I-$\alpha$-Bungarotoxin (BTX) Binding to Rat Hippocampal Membranes Rat brain cell membranes bearing $\alpha_7$ nAChR receptors may be prepared by homogenizing hippocampus tissue in 20 volumes of cold homogenization buffer (HB): mM concentrations of HB constituents:tris(hydroxymethyl)aminomethane 50; $CaCl_2$ 2; $MgCl_2$ 1; NaCl 120; KCl 5: pH 7.4). Homogenates are centrifuged for 5 minutes at 1000×g, the supernatant saved and the pellets re-extracted and centrifuged. Pooled supernatants are centrifuged for 20 minutes at 12,000×g, the pelleted membranous material is washed, and re-suspended in HB. Membranes (30-150 µg) are incubated with 3 nM [$^{125}$I]$\alpha$-BTX, 1 mg/mL bovine serum albumin (BSA), together with test compounds in HB for 2 hours at room temperature with gentle shaking. Membranes may then be trapped on Whatman glass fiber filters (thickness C or B) using a Brandel cell harvester and washed 4 times. Pre-treating the filters for 3 hours with 1% (BSA/0.01% PEI (polyethyleneimine) in water will yield low filter blanks (0.07% of total counts per minute). Non-specific binding may be determined by 100 µM (−)-nicotine. Typically specific binding is about 75%.

Assay for Affinity at Human $\alpha_7$ nAChR Receptor by Measuring the Binding of $^{125}$I-$\alpha$-Bungarotoxin (BTX) Binding to Membranes Membranes may be prepared from HEK cells expressing human $\alpha_7$ receptors by isolating a 500-40000×g membrane fraction. Such membranes may be used as described for rat brain membranes to assess the binding of compounds to human $\alpha_7$ receptors.

Analysis of Binding Data Obtained in $\alpha_7$ nAChR Receptor Assays $IC_{50}$ values and pseudo Hill coefficients ($n_H$) may be calculated using the non-linear curve-fitting program ALLFIT (DeLean A, Munson P J and Rodbard D (1977) Am. J. Physiol., 235:E97-E102). Saturation curves may be fitted to a one site model, using the non-linear regression program ENZFITTER (Leatherbarrow, R. J. (1987)), yielding a Kd value for [$^{125}$I]-$\alpha$-BTX binding to rat $\alpha$7 nAChR of 1.7 nM. $K_i$ values may be estimated using the general Cheng-Prusoff equation:

$$K_i = [IC_{50}]/((2+([ligand]/K_D)^n)^{1/n} - 1)$$

where a value of n=1 is used whenever $n_H < 1.5$ and a value of n=2 is used when $n_H \geq 1.5$. To account for variability, assays may be performed in triplicate and variability will typically be ±5%. $K_i$ values may be determined using six to 11 drug concentrations.

Compounds of the invention expected to have useful therapeutic activity will be found to have binding affinities ($K_i$) of less than 10 µM in $\alpha_7$ nAChR receptor assays.

The compounds of the invention have the advantage that they may be less toxic, be more efficacious, be longer acting, have a broader range of activity, be more potent, produce fewer side effects, are more easily absorbed or have other useful pharmacological properties.

General Experimental Procedures and Conditions

Commercial reagents were used without further purification. Mass spectra were recorded as m/z for the parent molecular ion unless specified otherwise. Room temperature (rt) refers to 20-25° C.

Microwave heating was achieved with a Personal Chemistry Smith Synthesizer or a Personal Chemistry Emrys Optimizer (monomodal, 2.45 GHz, 300 W max). Supercritical Fluid Chromatography (SFC) may have been performed as a means of purification for selected compounds and intermediates.

LCMS HPLC method was generally performed with an Agilent Zorbax 5µ SB-C8 column 2.1 mm×5 cm. Solvents: A=$H_2O$ with 2% ACN and 0.1% formic acid, B=2% $H_2O$ with 98% ACN and 0.05% formic acid. Gradient: (0% B through 0.5 min., 60% B at 3 min., 95% B at 6 min.).

Abbreviations Used

ACN acetonitrile
AcOH acetic acid
DCE 1,2-dichloroethane
DME 1,2-dimethoxyethane
ES$^+$ electrospray
EtOAc ethyl acetate
EtOH ethanol
$Et_2O$ diethyl ether
h hours
Hz hertz
HPLC high performance liquid chromatography
LCMS Liquid Chromatography Mass Spectrometry
MeOH methanol
min minutes
MS mass spectrometry
m/z mass to charge
nBuLi n-butyllithium
rt room temperature
NMR nuclear magnetic resonance
THF tetrahydrofuran Methods of Preparation Methods that may be used for the synthesis of compounds of Formula I, include the procedures illustrated in Scheme 1 and processes analogous to those described in the Examples. In Scheme 1 X, n, $R^1$ and R2 are as defined for compounds of Formula I.

conditions for such procedures are known in the art. Specific examples of procedures which may be employed include, but are not limited to, electrophilic functionalization of an aromatic ring, for example by nitration, halogenation, or acylation; transformation of a nitro group to an amino group, for example by reduction, such as by catalytic hydrogenation;

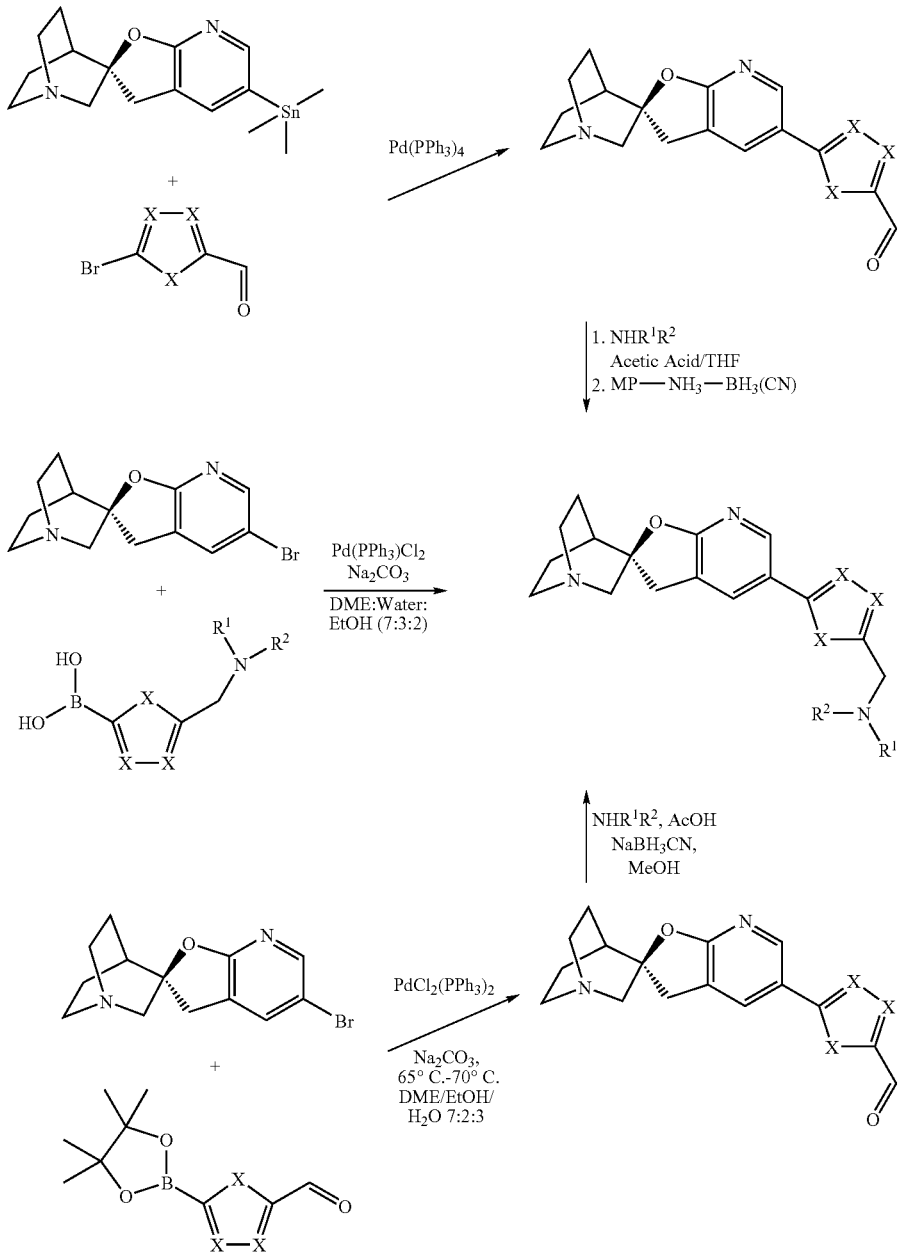

Scheme 1

It will be appreciated by those skilled in the art that aromatic substituents in the compounds of the invention, or in intermediates used in the synthesis of compounds of the invention, may be introduced by employing aromatic substitution reactions, functional group transformations to modify existing substituents, or a combination thereof. Such reactions may be effected either prior to or immediately following the processes mentioned above. The reagents and reaction acylation, alkylation, sulfonylation of an amino or hydroxyl group; replacement of an amino group by another functional group by conversion to an intermediate diazonium salt followed by nucleophilic or free radical substitution of the diazonium salt; or replacement of a halogen by another functional group, for example by nucleophilic or organometallically-catalysed substitution reactions.

EXAMPLES

Example 1

N,N-dimethyl-1-{5-[(2R)-3'H-spiro[4-azabicyclo[2.2.2]octane-2,2'-furo[2,3-b]pyridin]-5'-yl]-2-thienyl}methenamine

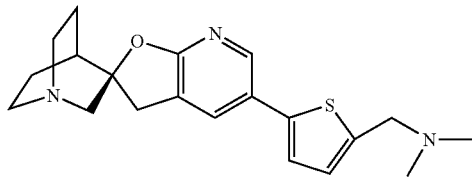

a) {5-[(dimethylamino)methyl]-2-thienyl}boronic acid

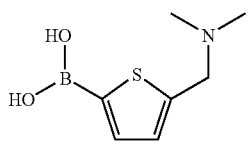

To a suspension of 5-formyl-2-thiopheneboronic acid (500 mg, 3.2 mmol) in DCE (30 mL) was added dimethylamine hydrochloride (520 mg, 6.3 mmol) followed by triethylamine (0.9 mL, 6.5 mmol). The reaction mixture was stirred for 10 min before sodium triacetoxyborohydride (1.36 g, 6.3 mmol) was added in one portion. After the reaction mixture was stirred at room temperature for 5 h, it was quenched with 30 mL of MeOH, stirred briefly, then concentrated under vacuum. Introduction of a $CH_2Cl_2/Et_2O$ mixture to this residue revealed a solid, which was filtered and washed with $Et_2O$. The resulting organic filtrate was concentrated to a viscous oil, which was used without further purification.

b) To a solution of {5-[(dimethylamino)methyl]-2-thienyl}boronic acid (2.23 mmol) in 10 mL of a $DME:H_2O:EtOH$ mixture (7:3:2) was added (2R)-5'-bromo-3'H-spiro[4-azabicyclo[2.2.2]octane-2,2'-furo[2,3-b]pyridine] (330 mg, 1.11 mmol). The reaction mixture was stirred for several minutes until homogeneous, at which point $Pd(PPh_3)_2Cl_2$ (77 mg, 0.11 mmol) was added followed by solid $Na_2CO_3$ (945 mg, 8.92 mmol). The reaction mixture was purged with $N_2$ and heated at 65° C. overnight. The reaction mixture was concentrated by rotary evaporation, then partitioned between water and $CHCl_3$. The organic layer was isolated and the aqueous layer was extracted 4×50 mL $CHCl_3$. The combined organic layer was washed with brine, dried ($Na_2SO_4$), filtered and concentrated to a viscous oil. The product was chromatographed through silica gel and eluted using 9.5:0.5 $CHCl_3$ and 7.0 M ammonia in methanol. The title compound was further purified by trituration in ether and isolated as a solid (150 mg). $^1H$ NMR (500 MHz, $CD_3OD$) δ 1.58-1.65 (m, 1H), 1.74-1.83 (m, 2H), 2.04 (bs, 1H), 2.14-2.24 (m, 1H), 2.29 (s, 6H), 2.81-2.87 (m, 2H), 2.92-2.98 (m, 2H), 3.07 (d, J=16 Hz, 1H), 3.18 (d, J=17 Hz, 1H), 3.28 (d, J=16 Hz, 1H), 3.54 (d, J=17 Hz, 1H), 3.68 (s, 2H), 6.94 (d, J=3.6 Hz, 1H), 7.16 (d, J=3.6 Hz, 1H), 7.84 (d, J=2.4 Hz, 1H), 8.14 (d, J=2.4 Hz, 1H) MS $ES^{(+)}$, m/z=356 (M+Na).

Example 2

N,N-dimethyl-1-{5-[(2R)-3'H-spiro[4-azabicyclo[2.2.2]octane-2,2'-furo[2,3-b]pyridin]-5'-yl]-2-furyl}methenamine

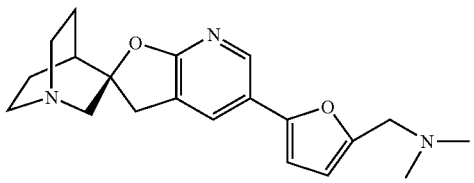

a) {5-[(dimethylamino)methyl]-2-furyl}boronic acid

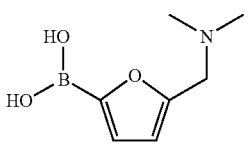

To a solution of (5-formyl-2-furyl)boronic acid (50 mg, 0.36 mmol) in DME (1.0 mL) was added a 2.0M solution of dimethylamine in THF (0.53 mL, 1.0 mmol). The reaction mixture stirred for 5 minutes before resin bound MP-BH$(OAc)_3$ (2.2 mmol/g, 0.33 g, 0.714 mmol) was added. The reaction mixture was stirred at room temperature for five hours and an additional 1 equivalent of dimethylamine in THF was added and stirring continued overnight. The reaction mixture was filtered through a plug of glass wool and the resin was washed with DME. The THF/DME filtrate solution containing the desired compound was used immediately in subsequent reactions.

b) To a solution of {5-[(dimethylamino)methyl]-2-furyl}boronic acid (0.25 mmol) in 2.5 mL of a $DME:H_2O:EtOH$ mixture (7:3:2) was added (2R)-5'-bromo-3'H-spiro[4-azabicyclo[2.2.2]octane-2,2'-furo[2,3-b]pyridine] (37 mg, 0.12 mmol). The reaction mixture was stirred for several minutes until homogeneous, at which point $Pd(PPh_3)_2Cl_2$ (9 mg, 0.012 mmol) was added followed by solid $Na_2CO_3$ (53 mg, 0.5 mmol). The reaction mixture was purged with $N_2$ and heated at 65° C. for 4.5 h. The reaction mixture was partitioned between water and $CHCl_3$. The organic layer was isolated and the aqueous layer was extracted 2×50 mL $CHCl_3$. The combined organic layer was washed with brine, dried ($Na_2SO_4$), filtered and concentrated. The product was purified by preparative plate chromatography using 9.0:1.0 $CHCl_3$ and 7.0 M ammonia in methanol as the eluant. The title compound was isolated as viscous oil (30 mg). $^1H$ NMR (500 MHz, $CD_3OD$) δ 1.59-1.63 (m, 1H), 1.73-1.82 (m, 2H), 2.04 (bs, 1H), 2.18-2.22 (m, 1H), 2.29 (s, 6H), 2.83-2.86 (m, 2H), 2.92-2.95 (m, 2H), 3.06 (d, J=16 Hz, 1H), 3.18 (d, J=16 Hz, 1H), 3.26 (d, J=16 Hz, 1H), 3.54 (d, J=16 Hz, 1H), 3.68 (s, 2H), 6.38 (d, J=3.2 Hz, 1H), 6.66 (d, J=3.2 Hz, 1H), 7.91 (d, J=2 Hz, 1H), 8.26 (d, J=2 Hz, 1H) MS $ES^{(+)}$, m/z=340 (M+Na).

Alternatively, N,N-dimethyl-1-{5-[(2R)-3'H-spiro[4-azabicyclo[2.2.2]octane-2,2'-furo[2,3-b]pyridin]-5'-yl]-2-furyl}methenamine can be prepared via the aldehyde by the method given below.

a) 5-[(2R)-3'H-spiro[4-azabicyclo[2.2.2]octane-2,2'-furo[2,3-b]pyridin]-5'-yl]-2-furaldehyde

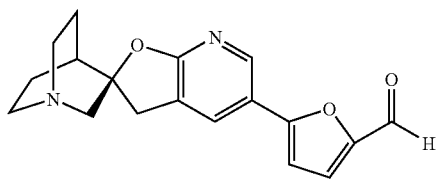

To a solution of (2R)-5'-bromo-3'H-spiro[4-azabicyclo[2.2.2]octane-2,2'-furo[2,3-b]pyridine] (6 g, 20.3 mmol) in 400 mL of a DME:H$_2$O:EtOH mixture (7:3:2) was added 5-formyl-2-furanboronic acid (5.67 g, 40.5 mmol). The reaction mixture was purged with N$_2$ (directly into the solvent) and stirred for ten minutes until homogeneous. Solid Na$_2$CO$_3$ (8.6 g, 81.0 mmol) was added to the reaction mixture followed by Pd(PPh$_3$)$_2$Cl$_2$ (711 mg, 1.0 mmol). The reaction mixture was again purged with N$_2$ for 10 min, then heated at 65° C. for 6 h. The reaction mixture was stirred at rt overnight, then concentrated via rotary evaporator. The resulting residue was diluted with CHCl$_3$ and filtered through diatomaceous earth. The CHCl$_3$ filtrate was concentrated and the resulting residue was diluted with 1N HCl and extracted with EtOAc (3×150 mL). The acidic aqueous layer was made basic with the addition of 2N aqueous NaOH (to pH~12) and the basic aqueous solution was extracted with CHCl$_3$ (3×150 mL). The combined CHCl$_3$ layer was washed with brine, dried (Na$_2$SO$_4$), filtered and concentrated to a solid (5.79 g, 92% yield). This material was used without further purification. $^1$H NMR (500 MHz, CDCl$_3$) δ 1.46-1.53 (m, 1H), 1.68-1.71 (m, 2H), 2.03-2.04 (m, 1H), 2.22-2.26 (m, 1H), 2.78-2.94 (m, 3H), 2.97 (d, J=14.7 Hz, 1H), 3.00-3.04 (m, 1H), 3.07 (d, J=16.5 Hz, 1H), 3.40 (d, J=14.7 Hz, 1H), 3.47 (d, J=16.5 Hz, 1H), 6.74 (d, J=3.7 Hz, 1H), 7.30 (d, J=3.7 Hz, 1H), 7.89 (s, 1H), 8.48 (s, 1H), 9.62 (s, 1H) MS ES$^+$, m/z=311 (M+H$^+$).

b) N,N-dimethyl-1-{5-[(2R)-3'H-spiro[4-azabicyclo[2.2.2]octane-2,2'-furo[2,3-b]pyridin]-5'-yl]-2-furyl}methenamine To a solution of 5-[(2R)-3'H-spiro[4-azabicyclo[2.2.2]octane-2,2'-furo[2,3-b]pyridin]-5'-yl]-2-furaldehyde (5.8 g, 18.7 mmol) in methanol (180 mL) at room temperature under N$_2$ was added dimethylamine (18.7 mL of a 2.0 M THF solution, 37.3 mmol). The reaction mixture was stirred for 30 min at rt before AcOH (4.3 mL, 74.7 mmol) was added followed by the portionwise addition of NaBH$_3$CN (1.74 g, 28.0 mmol). The reaction mixture was then stirred at rt for 4 h, then concentrated via rotary evaporation. The resulting residue was diluted with saturated aqueous K$_2$CO$_3$ and extracted with CHCl$_3$ (4×100 mL). The combined CHCl$_3$ layer was washed with brine, dried (Na$_2$SO$_4$), filtered and concentrated to a viscous residue. The product was purified by column chromatography (SiO$_2$) using 9.5:0.5 CHCl$_3$ and 7.0 M ammonia in MeOH to elute the desired compound.

Example 3

N,N-dimethyl-1-{4-[(2R)-3'H-spiro[4-azabicyclo[2.2.2]octane-2,2'-furo[2,3-b]pyridin]-5'-yl]-2-thienyl}methenamine

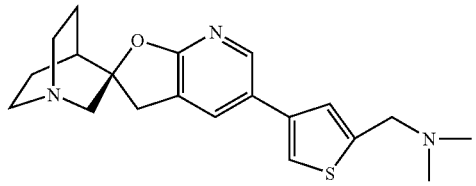

The compound of Example 3 was prepared by a process analogous to that used for Example 1, as detailed below.

a) 1-(4-bromo-2-thienyl)-N,N-dimethylmethanamine

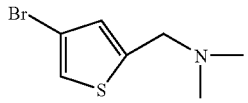

To a solution of 4-bromothiophene-2-carboxyaldehyde (5 g, 26.3 mmol) in EtOH (130 mL) at rt and under N$_2$ was added the dimethylamine in THF (20 mL of a 2.0 M solution, 40 mmol) followed by AcOH (1.9 mL). NaBH$_3$CN (2.1 g, 34 mmol) was then added in portions to the reaction mixture over a 5 min period and the reaction mixture was stirred overnight at rt. The reaction mixture was diluted with saturated NaHCO$_3$ and extracted with CHCl$_3$ (3×50 mL). The combined organic layer was concentrated and the resulting residue was diluted with 1 N HCl and washed with CHCl$_3$. The acidic aqueous layer was then made basic with the addition of saturated NaHCO$_3$ and extracted with CHCl$_3$ (3×50 mL). The combined organic layer was washed with brine, dried (Na$_2$SO$_4$), filtered and concentrated (86% yield). The product was used without further purification. $^1$H NMR (500 MHz, CD$_3$OD) δ 2.26 (s, 6H), 3.65 (s, 2H), 6.92 (apparent s, 1H), 7.31 (d, J=2 Hz, 1H).

b) Diisopropyl {5-[(dimethylamino)methyl]-3-thienyl}boronate

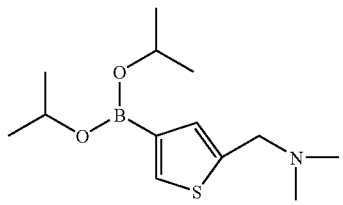

To a solution of 1-(4-bromo-2-thienyl)-N,N-dimethylmethanamine (2.8 g, 12.8 mmol) in THF (130 mL) at −78° C. under N$_2$ was added tri-isopropylborate (4.4 mL, 19.2 mmol). The reaction mixture was stirred briefly before nBuLi (12 mL of a 1.6 M hexane solution) was added dropwise via syringe. The reaction mixture then stirred for 6.5 h at −78° C. before being concentrated by rotary evaporation. The resulting white solid was used without further purification.

c) N,N-dimethyl-1-{4-[(2R)-3'H-spiro[4-azabicyclo [2.2.2]octane-2,2'-furo[2,3-b]pyridin]-5'-yl]-2-thienyl}methenamine

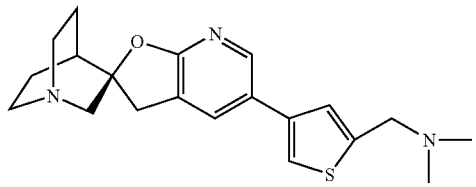

To a solution of diisopropyl {5-[(dimethylamino)methyl]-3-thienyl}boronate (3.6 g, 13 mmol) in 120 mL of a DME:H$_2$O:EtOH mixture (7:3:2) was added (2R)-5'-bromo-3'H-spiro[4-azabicyclo[2.2.2]octane-2,2'-furo[2,3-b]pyridine] (2.0 g, 6.75 mmol). The reaction mixture was purged with N$_2$ and stirred for several min until homogeneous, at which point Na$_2$CO$_3$ (2.9 g, 27 mmol) was added, followed by Pd(PPh$_3$)$_2$Cl$_2$ (236 mg, 0.34 mmol). The reaction mixture was purged with N$_2$ for 10 min, then heated at 75° C. for 2 h and at rt overnight. The reaction mixture was concentrated by rotary evaporation. The resulting residue was diluted with CHCl$_3$ and filtered though diatomaceous earth. The organic filtrate was concentrated and the resulting residue was diluted with 1 N HCl and extracted with EtOAc (3 times). The acidic aqueous layer was then made basic with the addition of 2 N NaOH and extracted with CHCl$_3$ (4×100 mL). The combined organic layer was washed with brine, dried (Na$_2$SO$_4$), filtered and concentrated to a viscous oil. The product was chomatographed though silica gel and eluted using 9.5:0.5 CHCl$_3$ and 7.0 M ammonia in methanol. The title compound was further purified by trituration in Et$_2$O and isolated (1.5 g, 62% yield). $^1$H NMR (500 MHz, CD$_3$OD) δ 1.58-1.64 (m, 1H), 1.73-1.82 (m, 2H), 2.04 (bs, 1H), 2.18-2.24 (m, 1H), 2.30 (s, 6H), 2.83-2.86 (m, 2H), 2.93-2.98 (m, 2H), 3.06 (d, J=14.6 Hz, 1H), 3.18 (d, J=16.5 Hz, 1H), 3.26 (d, J=14.6 Hz, 1H), 3.54 (d, J=17 Hz, 1H), 3.71 (s, 2H), 7.28 (s, 1H), 7.50 (s, 1H), 7.88 (s, 1H), 8.17 (s, 1H) MS ES$^+$, m/z=356 (M+Na$^+$).

Example 4

N,N-dimethyl-1-{4-[(2R)-3'H-spiro[4-azabicyclo [2.2.2]octane-2,2'-furo[2,3-b]pyridin]-5'-yl]-2-furyl}methenamine

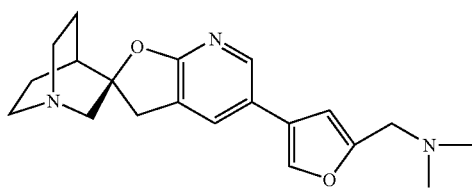

The compound of Example 4 may be prepared by a process analogous to that used for Example 2.

Example 5

N-methyl-1-{5-[(2R)-3'H-spiro[4-azabicyclo[2.2.2] octane-2,2'-furo[2,3-b]pyridin]-5'-yl]-2-thienyl}methanamine

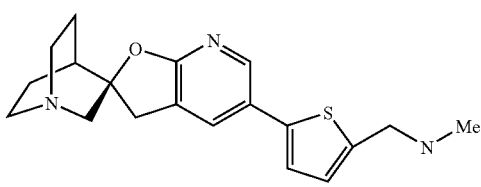

The compound of Example 5 may be prepared by a method analogous to the alternate method of Example 2, or prepared according to Scheme 2 as detailed below.

Scheme 2

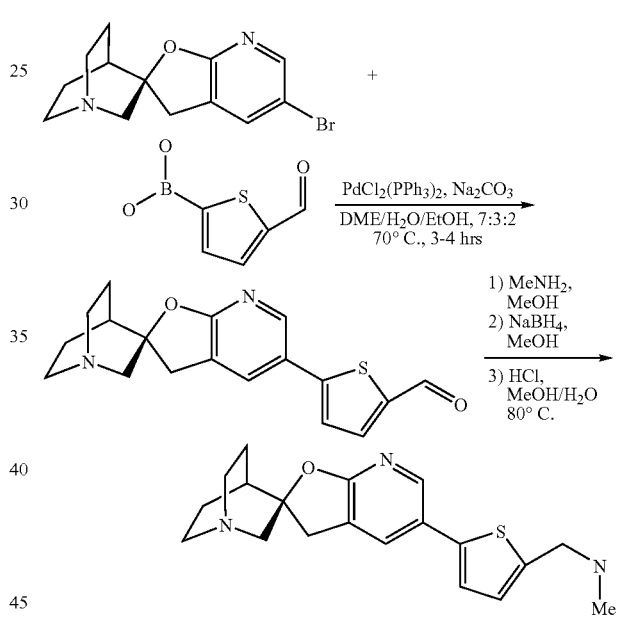

a) 5-[(2R)-3'H-spiro[4-azabicyclo[2.2.2]octane-2,2'-furo[2,3-b]pyridin]-5'-yl]thiophene-2-carbaldehyde To a stirred solution of (2R)-5'-bromo-3'H-spiro[4-azabicyclo[2.2.2]octane-2,2'-furo[2,3-b]pyridine] (Scheme 1, 3.2 g, 10.8 mmol) and (5-formyl-2-thienyl)boronic acid (3.37 g, 21.6 mmol) in 150 mL DME/H$_2$O/EtOH (7:3:2), powdered Na$_2$CO$_3$ (4.58 g, 43.2 mmol) was added. The resulting mixture was purged with N$_2$ at rt for 15 min, before the addition of dichloro[bis(triphenylphosphoranyl)]palladium (380 mg, 0.54 mmol). The reaction mixture was purged with N$_2$ for another 15 min, before being heated in a 70° C. oil bath under N$_2$ for 3-4 h. The reaction mixture was cooled and then concentrated under reduced pressure. The solid residue was treated with 150 mL CHCl$_3$, and the resulting suspension was filtered through a short pad of diatomaceous earth (the filter cake was washed with ~100 mL CHCl$_3$). The combined filtrate was concentrated under reduced pressure. The blackish solid was taken into 0.5 M HCl (100-150 mL) and EtOAc (~100 mL). The acidic aqueous layer was separated and the blackish organic layer was washed further with 0.5 M HCl (2×50 mL). The combined aqueous layers were then basified with 1 M NaOH to pH ~12, and extracted with CHCl₃ (100 mL, then 2×50 mL). The CHCl₃ extracts were dried over MgSO₄, filtered, and concentrated to give 3.5 g (99%) of 5-[(2R)-3'H-spiro[4-azabicyclo[2.2.2]octane-2,2'-furo[2,3-b]pyridin]-5'-yl]thiophene-2-carbaldehyde. ¹H NMR (500 MHz, CDCl₃) δ 1.50 (dddd, J=12.8, 10.7, 6.7, 2.3 Hz, 1H), 1.68-1.72 (m, 2H), 2.03 (t, J=2.9 Hz, 1H), 2.22-2.26 (m, 1H), 2.78-2.95 (m, 3H), 2.97 (dd, J=14.7, 2.1 Hz, 1H), 3.01-3.05 (m, 1H), 3.08 (d, J=16.5 Hz, 1H), 3.40 (dd, J=14.7, 1.6 Hz, 1H), 3.48 (d, J=16.5 Hz, 1H), 7.29 (d, J=4.0 Hz, 1H), 7.68 (d, J=2.2 Hz, 1H), 7.72 (d, J=4.0 Hz, 1H), 8.36 (d, J=2.2 Hz, 1H), 9.88 (s, 1H); MS ES⁺ m/z=327 (M+H⁺).

b) To a stirred suspension of 5-[(2R)-3'H-spiro[4-azabicyclo[2.2.2]octane-2,2'-furo[2,3-b]pyridin]-5'-yl]thiophene-2-carbaldehyde (1.5 g, 4.6 mmol) in 40 mL MeOH, 9.2 mL methylamine methanolic solution (18.4 mmol) was added. The clear solution was stirred at rt for 0.5 h before the addition of NaBH₄ (524 mg, 3.0 equiv) as one portion. The reaction mixture was stirred at rt for 1 h. The solution was concentrated under reduced pressure to give a black residue, which was dissolved in 60 mL MeOH and treated with 30 mL 4.0 M HCl. The resulting solution was heated at 80° C. for 1-2 h. MeOHl was removed under reduced pressure. The resulting acidic aqueous solution was basified by slow addition of conc. aqueous NaOH until pH>12 and extracted with CHCl₃ (3×50 mL). The blackish organic layers were dried over MgSO₄, filtered and concentrated to give a black residue, which was then purified by short-packed silica gel column (5% 7 M NH₃/MeOH in CHCl₃) to give a yellowish solid, which was washed with minimum amount of Et₂O (~20 mL) to remove minor impurities. Yield: 1.2 g (76%); ¹H NMR (500 MHz, CDCl₃) δ 1.48 (ddd, J=12.8, 10.7, 6.6, 2.3 Hz, 1H), 1.67-1.70 (m, 2H), 2.02 (t, J=2.9 Hz, 1H), 2.22-2.27 (m, 1H), 2.50 (s, 3H), 2.77-2.93 (m, 3H), 2.96 (dd, J=14.7, 2.1 Hz, 1H), 3.01-3.07 (m, 1H), 3.04 (d, J=16.2 Hz, 1H), 3.39 (dd, J=14.7, 1.8 Hz, 1H), 3.43 (d, J=16.2 Hz, 1H), 3.93 (s, 1H), 6.87 (d, J=3.6 Hz, 1H), 7.01 (d, J=3.6 Hz, 1H), 7.59 (d, J=2.2 Hz, 1H), 8.23 (d, J=2.2 Hz, 1H); MS ES⁺ m/z=342 (M+H⁺).

Example 6

N-methyl-1-{5-[(2R)-3'H-spiro[4-azabicyclo[2.2.2]octane-2,2'-furo[2,3-b]pyridin]-5'-yl]-2-furyl}methenamine

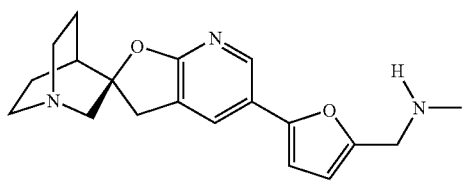

This compound was prepared by a process analogous to that used for Example 5, via Scheme 2. ¹H NMR (500 MHz, CDCl₃) δ 1.44-1.50 (m, 1H), 1.67-1.70 (m, 2H), 2.00-2.03 (m, 1H), 2.22-2.27 (m, 1H), 2.48 (s, 3H), 2.79-3.04 (m, 6H), 3.42 (d, J=16.3 Hz, 1H), 3.39 (d, J=15.6 Hz, 1H), 3.78 (s, 2H), 6.24 (d, J=3.1 Hz, 1H), 6.45 (d, J=3.1 Hz, 1H), 7.69 (s, 1H), 8.31 (s, 1H); MS ES⁺, m/z=326 (M+H⁺)

Example 7

(2R)-5'-[5-(pyrrolidin-1-ylmethyl)-2-furyl]-3'H-spiro[4-azabicyclo[2.2.2]octane-2,2'-furo[2,3-b]pyridine]

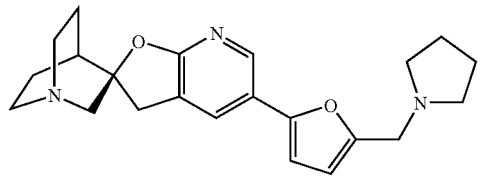

A process analogous to the alternate preparation for Example 2 was used to prepare this compound. ¹H NMR (300 MHz, CDCl₃) δ 1.42-1.52 (dddd, J=2.6, 6.8, 10.2, 12.8 Hz, 1H), 1.66-1.71 (m, 2H), 1.77-1.83 (m, 4H), 1.98-2.03 (m, 1H), 2.21-2.28 (m, 1H), 2.57-2.63 (m, 4H), 2.79-3.05 (m, 6H), 3.39 (d, J=14.6 Hz, 1H), 3.42 (d, J=16.3 Hz, 1H), 3.68 (s, 2H), 6.25 (d, J=3.2 Hz, 1H), 6.45 (d, J=3.2 Hz, 1H), 7.71 (d, J=2.2 Hz, 1H), 8.31 (d, J=2.2 Hz, 1H); MS ES⁺, m/z=366 (M+H⁺)

Example 8

(2R)-5'-[5-(morpholin-4-ylmethyl)-2-furyl]-3'H-spiro[14-azabicyclo[2.2.2]octane-2,2'-furo[2,3-b]pyridine]

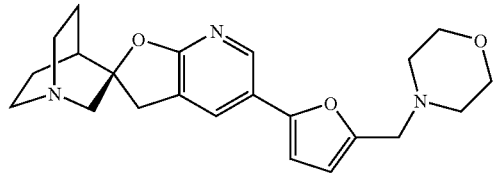

A process analogous to the alternate preparation for Example 2 was used to prepare this compound. ¹H NMR (300 MHz, CDCl₃) δ 1.42-1.50 (m, 1H), 1.66-1.71 (m, 2H), 2.00-2.04 (m, 1H), 2.20-2.28 (m, 1H), 2.53 (t, J=4.6 Hz, 4H), 2.82-3.06 (m, 6H), 3.39 (d, J=13.8 Hz, 1H), 3.43 (d, J=16.3 Hz, 1H), 3.59 (s, 2H), 3.73 (t, J=4.6 Hz, 4H), 6.28 (d, J=3.4 Hz, 1H), 6.46 (d, J=3.4 Hz, 1H), 7.70 (s, 1H), 8.32 (s, 1H); MS ES⁺, m/z=382 (M+H⁺).

Example 9

N,N-dimethyl-1-{4-[(2R)-3'H-spiro[4-azabicyclo[2.2.2]octane-2,2'-furo[2,3-b]pyridin]-5'-yl]-2-furyl}methenamine

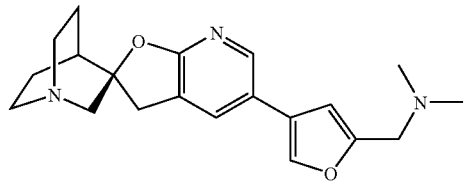

A process analogous to the alternate preparation for Example 2 was used to prepare this compound, utilizing 5-formylfuran-3-boronic acid pinacol ester in the Suzuki coupling in place of the free boronic acid. $^1$H NMR (500 MHz, CD$_3$OD) δ 1.57-1.63 (m, 1H), 1.72-1.82 (m, 2H), 2.04 (bs, 1H), 2.15-2.22 (m, 1H), 2.29 (s, 6H), 2.83-2.87 (m, 2H), 2.92-2.97 (m, 2H), 3.06 (d, J=14.6 Hz, 1H), 3.16 (d, J=17 Hz, 1H), 3.26 (d, J=14.6 Hz, 1H), 3.53 (d, J=18 Hz, 1H), 3.54 (s, 2H), 6.66 (s, 1H), 7.78 (d, J=2 Hz, 1H), 7.82 (s, 1H), 8.07 (d, J=2 Hz, 1H) MS ES$^+$, m/z=340 (M+Na$^+$).

Example 10

(2R)-5'-[5-(pyrrolidin-1-ylmethyl)-3-furyl]-3'H-spiro[4-azabicyclo[2.2.2]octane-2,2'-furo[2,3-b]pyridine]

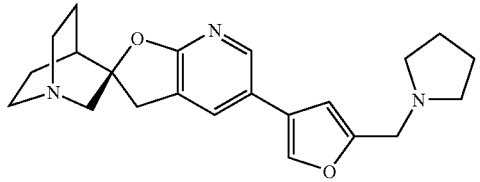

This compound was prepared by a process analogous to that used for Example 9, N,N-dimethyl-1-{4-[(2R)-3'H-spiro[4-azabicyclo[2.2.2]octane-2,2'-furo[2,3-b]pyridin]-5'-yl]-2-furyl}methenamine. $^1$H NMR (500 MHz, CD$_3$OD) δ 1.57-1.63 (m, 1H), 1.74-1.85 (m, 6H), 2.03 (bs, 1H), 2.17-2.22 (m, 1H), 2.62-2.64 (m, 4H), 2.81-2.87 (m, 2H), 2.92-2.97 (m, 2H), 3.06 (d, J=14.6 Hz, 1H), 3.16 (d, J=17 Hz, 1H), 3.26 (d, J=14.6 Hz, 1H), 3.53 (d, J=16.5 Hz, 1H), 3.69 (s, 2H), 6.64 (s, 1H), 7.77 (d, J=2 Hz, 1H), 7.81 (s, 1H), 8.07 (d, J=2 Hz, 1H) MS ES$^+$, m/z=366 (M+Na$^+$).

Example 11

(2R)-5'-[5-(morpholin-4-ylmethyl)-3-furyl]-3'H-spiro[4-azabicyclo[2.2.2]octane-2,2'-furo[2,3-b]pyridine]

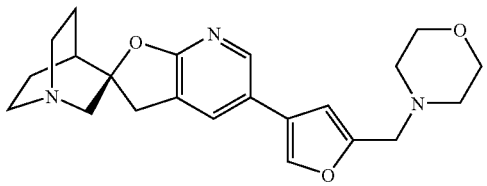

This compound was prepared by a process analogous to that used for Example 9, N,N-dimethyl-1-{4-[(2R)-3'H-spiro[4-azabicyclo[2.2.2]octane-2,2'-furo[2,3-b]pyridin]-5'-yl]-2-furyl}methenamine. $^1$H NMR (500 MHz, CD$_3$OD) δ 1.57-1.63 (m, 1H), 1.72-1.81 (m, 2H), 2.03 (bs, 1H), 2.18-2.22 (m, 1H), 2.51-2.53 (m, 4H), 2.80-2.86 (m, 2H), 2.92-2.97 (m, 2H), 3.06 (d, J=14.6 Hz, 1H), 3.16 (d, J=17 Hz, 1H), 3.26 (d, J=14.6 Hz, 1H), 3.53 (d, J=16.5 Hz, 1H), 3.59 (s, 2H), 3.68-3.70 (m, 4H), 6.66 (s, 1H), 7.77 (d, J=2 Hz, 1H), 7.82 (s, 1H), 8.07 (d, J=2 Hz, 1H) MS ES$^+$, m/z=382 (M+Na$^+$).

Example 12

N-methyl-N-({5-[(2R)-3'H-spiro[4-azabicyclo[2.2.2]octane-2,2'-furo[2,3-b]pyridin]-5'-yl]-2-furyl}methyl)cyclopropanamine

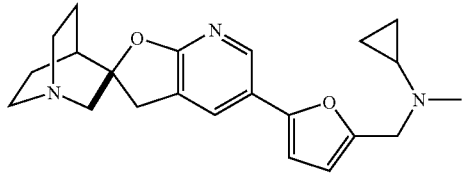

To a stirred solution of N-methyl-1-{5-[(2R)-3'H-spiro[4-azabicyclo[2.2.2]octane-2,2'-furo[2,3-b]pyridin]-5'-yl]-2-furyl}methenamine (140 mg, 0.4 mmol) as prepared in Example 6 in 7 mL MeOH, [(1-ethoxycyclopropyl)oxy](trimethyl)silane (410 mg) was added, followed by addition of AcOH (340 mg, 5.6 mmol) and NaBH$_3$CN (130 mg, 2.0 mmol). The reaction mixture was heated at 65° C. oil bath overnight. It was then cooled to rt and concentrated under reduced pressure. The residue was quenched with aqueous potassium carbonate solution and extracted with CHCl$_3$ (3×30 mL). The organic layers were combined, dried over MgSO$_4$, filtered and concentrated under reduced pressure. The residue was then purified by silica gel column chromatography (5% 7M NH$_3$/MeOH in CHCl$_3$) to give the title compound (90 mg, 62% yield). $^1$H NMR (500 MHz, CDCl$_3$) δ 0.41-0.49 (m, 4H), 1.47 (dddd, J=2.4, 6.7, 10.4, 12.8 Hz, 1H), 1.67-1.70 (m, 2H), 1.73 (m, 1H), 1.99-2.01 (m, 1H), 2.21-2.27 (m, 1H), 2.39 (s, 3H), 2.78-2.92 (m, 3H), 2.95 (dd, J=2.4, 14.7 Hz, 1H), 3.03 (d, J=16.5 Hz, 1H), 3.00-3.06 (m, 1H), 3.39 (d, J=14.7 Hz, 1H), 3.42 (d, J=16.5 Hz, 1H), 3.73 (s, 2H), 6.24 (d, J=3.3 Hz, 1H), 6.46 (d, J=3.3 Hz, 1H), 7.69 (d, J=1.8 Hz, 1H), 8.31 (d, J=1.8 Hz, 1H); MS ES$^+$, m/z=366 (M+H$^+$).

Example 13

N-methyl-N-({4-[(2R)-3'H-spiro[4-azabicyclo[2.2.2]octane-2,2'-furo[2,3-b]pyridin]-5'-yl]-2-furyl}methyl)cyclopropanamine

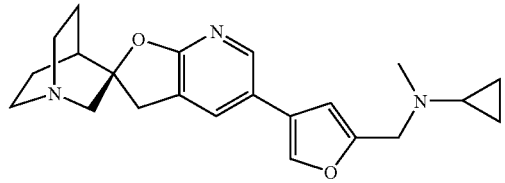

This compound was prepared by a process analogous to that used for Example 12. $^1$H NMR (500 MHz, CD$_3$OD) δ 0.40-0.42 (m, 2H), 0.49-0.51 (m, 2H), 1.58-1.63 (m, 1H), 1.74-1.82 (m, 3H), 2.04 (bs, 1H), 2.18-2.23 (m, 1H), 2.36 (s, 3H), 2.82-2.86 (m, 2H), 2.94-2.97 (m, 2H), 3.06 (d, J=16 Hz, 1H), 3.16 (d, J=16.5 Hz, 1H), 3.26 (d, J=15 Hz, 1H), 3.53 (d, J=16.5 Hz, 1H), 3.72 (s, 2H), 6.63 (s, 1H), 7.78 (d, J=2 Hz, 1H), 7.81 (s, 1H), 8.08 (d, J=2 Hz, 1H) MS ES$^+$, m/z=366 (M+Na$^+$).

The compounds of Examples 14, 15 and 16 may be prepared by the process of Scheme 1, or as specifically described.

Example 14

1-{5-[(2R)-3'H-spiro[4-azabicyclo[2.2.2]octane-2,2'-furo[2,3-b]pyridin]-5'-yl]-2-furyl}methenamine

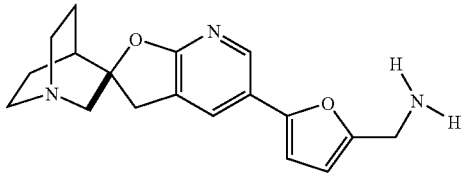

To a hydrogenation vessel, a spatula tip of Ra—Ni in aqueous suspension was added. The catalyst was washed with MeOH (2×2 mL), before the addition of 5 mL Methanolic solution of 100 mg (0.32 mmol) 5-[(2R)-3'H-spiro[4-azabicyclo[2.2.2]octane-2,2'-furo[2,3-b]pyridin]-5'-yl]-2-furaldehyde and 10 mL 7 M $NH_3$ in MeOH. The hydrogenation reaction was carried out in a Parr shaker (50 psi, 45° C., 2-3 h). The catalyst was filtered off, and the filtrate was concentrated under reduced pressure. The residue was then purified by silica gel column chromatography (18% MeOH, 2% $NH_4OH$ in $CHCl_3$ as eluent) to give the title compound (63 mg, 63% yield). $^1H$ NMR (500 MHz, $CDCl_3$) δ 1.44-1.51 (dddd, J=2.4, 6.7, 10.4, 12.8 Hz, 1H), 1.66-1.70 (m, 2H), 2.00-2.03 (m, 1H), 2.21-2.28 (m, 1H), 2.77-2.93 (m, 3H), 2.95 (dd, J=2.4, 14.7 Hz, 1H), 3.02 (d, J=16.5 Hz, 1H), 3.00-3.07 (m, 1H), 3.39 (d, J=14.7 Hz, 1H), 3.43 (d, J=16.5 Hz, 1H), 3.87 (s, 2H), 6.20 (d, J=3.4 Hz, 1H), 6.44 (d, J=3.4 Hz, 1H), 7.69 (s, 1H), 8.31 (s, 1H) MS $ES^+$, m/z=312 $(M+H^+)$.

Example 15

1-{5-[(2R)-3'H-spiro[4-azabicyclo[2.2.2]octane-2,2'-furo[2,3-b]pyridin]-5'-yl]-2-thienyl}methenamine

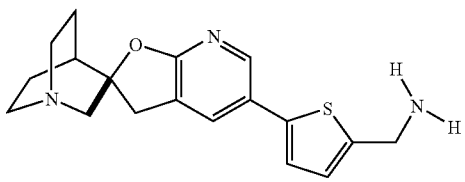

To a solution of 5-[(2R)-3'H-spiro[4-azabicyclo[2.2.2]octane-2,2'-furo[2,3-b]pyridin]-5'-yl]thiophene-2-carbaldehyde (326 mg, 1.0 mmol) in 10 mL MeOH, 0.2 mL 50% hydroxylamine aqueous solution (3.0 mmol) was added. The reaction mixture was stirred at rt for 2 h, then was concentrated under reduced pressure to give the oxime intermediate (300 mg, 88%), which was used without any further purification.

To a stirred solution of oxime (280 mg, 0.8 mmol) in AcOH (4 mL), Zn powder (390 mg, 6 mmol) was added. The reaction mixture was stirred at rt for 1 h (progress was monitored by LCMS). It was then diluted with MeOH and filtered. The filtrate was concentrated under reduced pressure. The residue was quenched with aqueous potassium carbonate solution and extracted with $CHCl_3$ (3×30 mL). The organic layers were combined, dried over $MgSO_4$, filtered and concentrated under reduced pressure. The residue was then purified by silica gel column chromatography (18% MeOH, 2% $NH_4OH$ in $CHCl_3$ as eluent) to give the title compound (0.26 g, 99% yield). $^1H$ NMR (500 MHz, $CDCl_3$) δ 1.47 (dddd, J=2.4, 6.7, 10.4, 12.8 Hz, 1H), 1.68-1.71 (m, 2H), 2.01-2.04 (m, 1H), 2.23-2.27 (m, 1H), 2.78-2.93 (m, 3H), 2.96 (dd, J=2.4, 14.7 Hz, 1H), 3.01-3.07 (m, 1H), 3.04 (d, J=16.3 Hz, 1H), 3.40 (dd, J=1.2, 14.7 Hz, 1H), 3.44 (d, J=16.3 Hz, 1H), 4.05 (s, 2H), 6.86 (d, J=3.6 Hz, 1H), 7.01 (d, J=3.6 Hz, 1H), 7.59 (s, 1H), 8.22 (s, 1H); MS $ES^+$, m/z=328 $(M+H^+)$

Example 16

1-{4-[(2R)-3'H-spiro[4-azabicyclo[2.2.2]octane-2,2'-furo[2,3-b]pyridin]-5'-yl]-2-furyl}methenamine

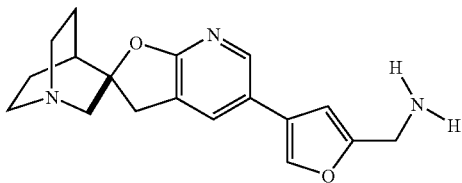

This compound was prepared by a process analogous to that used for Example 15. $^1H$ NMR (300 MHz, $CD_3OD$) δ 1.55-1.65 (m, 1H), 1.69-1.87 (m, 2H), 2.03 (s, 1H), 2.12-2.25 (m, 1H), 2.81-2.97 (m, 2H), 3.06 (d, J=14.7 Hz, 1H), 3.15 (d, J=16.7 Hz, 1H), 3.27 (d, J=14.7 Hz, 1H), 3.51 (d, J=16.7 Hz, 1H), 3.80 (s, 2H), 6.59 (s, 1H), 7.74 (d, J=1.8 Hz, 1H), 7.79 (s, 1H), 8.05 (d, J=1.8 Hz, 1H); MS $ES^+$ m/z=312 $(M+H^+)$

The invention claimed is:

1. A compound that is (2R)-5'-[5-(morpholin-4-ylmethyl)-3-furyl]-3'H-Spiro[4-azabicyclo[2.2.2]octane-2,2'-furo[2,3-b]pyridine] or a pharmaceutically acceptable salt thereof.

2. A pharmaceutically acceptable salt according to claim 1 that is a hydrochloride, a hydrobromide, a formate, an acetate, a maleate, a benzoate, a tartrate, or a fumarate.

3. A pharmaceutical composition comprising a compound or a pharmaceutically acceptable salt thereof according to claim 1 and at least one pharmaceutically acceptable diluent, lubricant or carrier.

4. A pharmaceutical composition comprising a pharmaceutically acceptable salt according to claim 2 and at least one pharmaceutically acceptable diluent, lubricant or carrier.

* * * * *